(12) United States Patent
Garstka et al.

(10) Patent No.: US 9,433,658 B2
(45) Date of Patent: *Sep. 6, 2016

(54) MEDICAL ELECTRODE

(71) Applicant: COVIDIEN LP, Mansfield, MA (US)

(72) Inventors: Erick Garstka, Westfield, MA (US); Kathleen Tremblay, Westfield, MA (US)

(73) Assignee: Covidien LP, Mansfield, MA (US)

( * ) Notice: Subject to any disclaimer, the term of this patent is extended or adjusted under 35 U.S.C. 154(b) by 213 days.

This patent is subject to a terminal disclaimer.

(21) Appl. No.: 14/010,877

(22) Filed: Aug. 27, 2013

(65) Prior Publication Data

US 2014/0065248 A1    Mar. 6, 2014

Related U.S. Application Data

(63) Continuation of application No. 12/855,292, filed on Aug. 12, 2010, now Pat. No. 8,548,557.

(51) Int. Cl.
*A61N 1/04* (2006.01)
*A61K 36/896* (2006.01)
*A61B 5/0408* (2006.01)
*A61B 5/0478* (2006.01)
*A61K 31/045* (2006.01)
*A61K 31/125* (2006.01)

(52) U.S. Cl.
CPC .......... *A61K 36/896* (2013.01); *A61B 5/0478* (2013.01); *A61B 5/04087* (2013.01); *A61K 31/045* (2013.01); *A61K 31/125* (2013.01); *A61N 1/0472* (2013.01); *A61N 1/046* (2013.01); *A61N 1/0428* (2013.01); *A61N 1/0452* (2013.01); *A61N 1/0456* (2013.01); *A61N 1/0464* (2013.01); *A61N 1/0468* (2013.01)

(58) Field of Classification Search
CPC ............ A61B 5/04087; A61B 5/0478; A61N 1/0472; A61N 1/0428; A61N 1/0456; A61N 1/0464; A61N 1/0452; A61N 1/046; A61N 1/0468; A61K 31/125; A61K 31/045; A61K 36/896
USPC ................... 252/519.33, 519.32, 519.3, 500; 600/391, 392, 395, 397; 607/152
See application file for complete search history.

(56) References Cited

U.S. PATENT DOCUMENTS

| 4,226,247 A | 10/1980 | Hauser et al. |
|---|---|---|
| 4,657,023 A | 4/1987 | Kuhn |
| 4,675,009 A | 6/1987 | Hymes et al. |
| 4,699,146 A | 10/1987 | Sieverding |
| 4,717,378 A | 1/1988 | Perrault et al. |
| 4,768,523 A | 9/1988 | Cahalan et al. |
| 4,911,855 A | 3/1990 | Rasicci et al. |
| 5,143,071 A | 9/1992 | Keusch et al. |
| 5,173,302 A | 12/1992 | Holmblad et al. |
| 5,234,992 A | 8/1993 | Gyory et al. |
| 5,338,490 A | 8/1994 | Dietz et al. |
| 5,354,790 A | 10/1994 | Keusch et al. |
| 5,405,366 A | 4/1995 | Fox et al. |
| 5,660,178 A | 8/1997 | Kantner et al. |
| 5,674,275 A | 10/1997 | Tang et al. |
| 5,721,313 A | 2/1998 | Yeung et al. |
| 5,779,632 A | 7/1998 | Dietz et al. |
| 5,985,990 A | 11/1999 | Kantner et al. |
| 6,038,464 A | 3/2000 | Axelgaard et al. |
| 6,263,226 B1 | 7/2001 | Axelgaard et al. |
| 6,447,798 B1 | 9/2002 | Munro et al. |
| 6,544,258 B2 | 4/2003 | Fleenor et al. |
| 6,592,898 B2 | 7/2003 | Munro et al. |
| 6,613,030 B1 | 9/2003 | Coles et al. |
| 6,641,569 B1 | 11/2003 | Coles et al. |
| 6,683,120 B2 | 1/2004 | Munro |
| 6,792,301 B2 | 9/2004 | Munro et al. |
| 6,842,636 B2 | 1/2005 | Perrault et al. |
| 6,887,917 B2 | 5/2005 | Yang et al. |
| 6,987,133 B2 | 1/2006 | Chen |
| 7,076,282 B2 | 7/2006 | Munro et al. |
| 7,346,380 B2 | 3/2008 | Axelgaard et al. |
| 7,620,439 B2 | 11/2009 | Menon et al. |
| 7,699,840 B2 | 4/2010 | Eisele |
| 8,548,557 B2 * | 10/2013 | Garstka ............. A61B 5/04087 600/391 |
| 2003/0232895 A1 | 12/2003 | Omidian et al. |
| 2005/0085706 A1 | 4/2005 | Perrault et al. |
| 2005/0136077 A1 | 6/2005 | Yahiaoui et al. |

(Continued)

FOREIGN PATENT DOCUMENTS

EP    2055347 A1 *  5/2009  ......... A61B 5/04087
WO    88/05666 A1   8/1988

(Continued)

OTHER PUBLICATIONS

Examiner's Report dated Jan. 13, 2015 from Canadian Appl. No. 2642430.
Extended European Search Report issued in Appl. No. EP 077795018.6 dated Mar. 4, 2014.
Search Report from corresponding PCT Application No. PCT/US2011/046560 mailed Feb. 1, 2012.
Monroe, B.M., et al. "Photoinitiators for Free-Radical Initiated Photoimaging Systems," Chem.Rev., vol. 93, pp. 435-448 (1993).
Office Action issued in U.S. Appl. No. 12/208,424 mailed Mar. 5, 2009 (8 pages).

(Continued)

*Primary Examiner* — Douglas McGinty

(57) ABSTRACT

The present disclosure provides electrodes that possess hydrogels for contacting skin. In embodiments, an electrode of the present disclosure may include a substrate and a conductive composition on at least a portion of a surface of the substrate, the conductive composition including at least one hydrogel and at least one component capable of providing either a cooling or warming sensation upon electrical stimulation. Methods for forming these hydrogels and electrodes are also provided.

25 Claims, 2 Drawing Sheets

(56) References Cited

U.S. PATENT DOCUMENTS

| | | |
|---|---|---|
| 2005/0277991 A1 | 12/2005 | Covey et al. |
| 2006/0182788 A1 | 8/2006 | Singh et al. |
| 2007/0208130 A1 | 9/2007 | Sasahara et al. |
| 2007/0282188 A1 | 12/2007 | Copp-Howland |
| 2007/0282408 A1 | 12/2007 | Coggins |
| 2007/0293751 A1 | 12/2007 | Axelgaard et al. |
| 2008/0038386 A1 | 2/2008 | Moza et al. |
| 2008/0268077 A1* | 10/2008 | Vielhaber ............... A61K 8/34 424/756 |
| 2008/0305054 A1* | 12/2008 | Vielhaber ............. A61K 8/498 424/59 |
| 2009/0112283 A1* | 4/2009 | Kriksunov ............. A61N 1/205 607/46 |
| 2009/0270710 A1 | 10/2009 | Copp et al. |
| 2009/0298113 A1* | 12/2009 | Vielhaber .......... G01N 33/5088 435/29 |
| 2010/0228304 A1* | 9/2010 | Kriksunov ............. A61F 7/007 607/3 |
| 2011/0112605 A1* | 5/2011 | Fahey .................. A61N 1/0452 607/48 |
| 2011/0230816 A1 | 9/2011 | Copp-Howland |

FOREIGN PATENT DOCUMENTS

| | | |
|---|---|---|
| WO | 91/15250 A1 | 10/1991 |
| WO | 93/09713 A1 | 5/1993 |
| WO | 2007/063436 A1 | 6/2007 |
| WO | 2007/083275 A1 | 7/2007 |
| WO | 2007/142797 A2 | 12/2007 |

OTHER PUBLICATIONS

Office Action issued in U.S. Appl. No. 12/208,424 mailed Sep. 17, 2009 (8 pages).
Final Office Action issued in U.S. Appl. No. 12/208,424 mailed Apr. 13, 2010 (13 pages).
Claims from co-pending U.S. Appl. No. 12/208,424 (8 pages).
Search Report from corresponding European Application No. EP 10 16 0096 mailed Apr. 4, 2011.
The Examination Report issued in Application No. EP 11743745.9 dated Jun. 13, 2014.
Examination Report from Application No. EP 11743745.9 dated Feb. 23, 2015.

\* cited by examiner

MEDICAL ELECTRODE

CROSS-REFERENCE TO RELATED APPLICATIONS

This application is a continuation of U.S. patent application Ser. No. 12/855,292, filed Aug. 12, 2010, now U.S. Pat. No. 8,548,557, the entire disclosure of which is hereby incorporated by reference herein.

TECHNICAL FIELD

The present disclosure relates to hydrogels suitable for use as conductive compositions, methods of making these compositions, and the use of these compositions with medical electrodes.

BACKGROUND OF RELATED ART

Hydrogels constitute a broad class of materials which may be completely water soluble or swell extensively in water, but are not completely water soluble. They have been used in a variety of biomedical applications and may be applied in bulk forms which vary from clear to opaque, and from a relatively stiff to a relatively soft consistency. Sometimes the bulk forms are reinforced by reinforcement members which may be woven or non-woven fabrics to increase the composite strength and/or dimensional stability. Hydrogels have also been used as coatings for various biomedical applications.

Medical electrodes are used to transmit electrical signals or currents between the body of a patient and external medical equipment. These electrodes may include a conductive composition adhered to or otherwise in contact with, the skin of the patient, and a conductor, which is electrically connected to the conductive composition and to the external medical equipment.

Hydrogels for use as conductive compositions with medical electrodes remain desirable.

SUMMARY

The present disclosure provides electrodes that possess components capable of enhancing patient comfort upon application of an electrode to tissue, including skin.

In embodiments, an electrode of the present disclosure may include a substrate and a conductive composition on at least a portion of a surface of the substrate, the conductive composition including at least one hydrogel and at least one component capable of providing either a cooling or warming sensation upon contact with tissue of a patient.

Where the hydrogel includes a warming component, the warming component may be present in an amount of from about 0.01% by weight to about 1% by weight of the hydrogel.

Where the hydrogel includes a cooling component, the cooling component may be present in an amount of from about 0.01% by weight to about 20% by weight of the hydrogel.

Hydrogels of the present disclosure may include electrolytes and other additives. Where the hydrogel includes an electrolyte, the electrolyte may be present in an amount of from about 0.1% by weight to about 15% by weight of the hydrogel.

Methods for producing electrodes and the components thereof are also provided, as are methods for their use.

DETAILED DESCRIPTION

Figure 1:
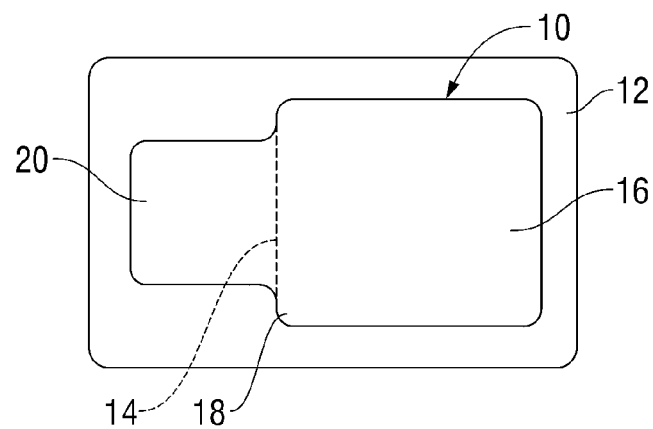
FIG. 1 is a top plan view of a medical electrode including the conductive composition of the present disclosure.

Any adhesive application, including those involving tissue, are within the purview of the hydrogel compositions of the present disclosure. In embodiments, hydrogels may be utilized as adhesives and/or conductive compositions for medical electrodes. The hydrogels of the present disclosure may include components that provide either a cooling or warming sensation upon contact with tissue of a patient, which may be desirable for a patient.

As used herein, the term "hydrogel" may refer to a wide variety of polymer-based compositions. These materials may be synthesized for example from monomer(s) or from monomer(s) mixed with polymer(s) or cross-linked polymer solutions in water. They may be obtained by chemical modification of existing polymer(s) or by adding water to existing dry polymers.

Any biocompatible hydrogel may be utilized in accordance with the present disclosure. Generally speaking, a hydrogel according to the present disclosure may include a coherent, three-dimensional aqueous polymer system capable of imbibing water without liquefying. In embodiments, insolubility in water may be provided by crosslinking the hydrogel polymer. In embodiments, hydrogels or water-containing gels of the present disclosure may include water and various chemical substances including gelatin; polysaccharides; crosslinked acrylamide polymers, hydroxyethyl-methacrylate polymers; crosslinked polyhydroxyethylacrylate; polymerized, crosslinked 2-acrylamido-2-methylpropane sulfonic acid polymers or one of their salts such as the sodium or potassium type; crosslinked polyvinylpyrrolidone; polyacrylic acid; copolymers of the aforementioned monomers with each other, copolymers of the aforementioned monomers with other polymers such as polystyrene or other non-hydrogel-forming polymers, one or more salts of the foregoing, and combinations thereof.

For example, by cross-linking homopolymers of an acrylamide derivative such as 2-acrylamido-2-methylpropane-sulfonic acid or one of its salts, hydrogels may be formed. Copolymers thereof may also be formed in the same way with acrylamide. Cross-linked homopolymers of acrylic acid and of methacrylic acid, their salts and copolymers may also be formed, as may other acrylic cross-linked homopolymers and copolymers.

Hydrogels of the present disclosure derive their adhesive properties in part from their ability to absorb water. When a relatively dry body of hydrogel contacts moisture, such as the moisture in tissue, particularly internal tissue, or any other moist surface, it develops an aggressive adhesive nature. When the polymer of the hydrogel is crosslinked to an adequate degree, the bulk hydrogel is sufficiently strong, even when swelled with additional liquid, to provide adhesive support for pacing leads, thereby establishing extended connection of the lead to tissue. However, excessive cross-linking decreases the tack of the hydrogel. Too little cross-linking decreases its cohesive strength. Thus, in embodiments, a crosslinking agent may be utilized in forming the polymer suitable as a hydrogel of the present disclosure.

In some embodiments, a suitable hydrogel for use as a conductive composition may include a copolymer. Non-limiting examples of suitable copolymers may include a first monomer, such as a mixture of acrylic acid and a salt thereof, and a second monomer, such as one of more monomers selected from $CH_2=CHC(O)XR$, in which X is O or NH and R is an unsubstituted or substituted alkyl group of 1 to 5 carbon atoms. The hydrogel may also include water; an electrolyte or mixture of electrolytes; a polymerization initiator; a neutralizer a such as sodium hydroxide; optionally, a crosslinking agent; and optionally, a thickener.

In embodiments, a first monomer which may be used to form a copolymer for use in a hydrogel includes acrylic acid, a salt thereof, or a mixture thereof. The copolymer thus produced by polymerization includes acid acrylate moieties ($-CO_2H$ and/or $-CO_2M$, in which M is a cation such as sodium ion, potassium ion, lithium ion, ammonium or substituted ammonium ion, etc.) directly attached to the polymer backbone.

In embodiments, a copolymer utilized in a hydrogel of the present disclosure may include a second monomer which may be one of more monomers of the formula $CH_2=CHC(O)XR$, in which X is O or NH and R is an unsubstituted or substituted alkyl group of 1 to 5 carbon atoms. The polymer produced by this polymerization includes groups of the structure $-C(O)XR$ directly attached to the polymer backbone.

Suitable unsubstituted alkyl groups are methyl, ethyl, n-propyl, n-butyl, and n-pentyl. Suitable substituents that may be present in a substituted alkyl group are halo (such as F, Cl, or Br) cyano, carboxylic acid and salts thereof (i.e., $-CO_2H$ or $-CO_2M$, in which M is a cation), phosphate and salts thereof, and sulfonic acid and salts thereof. An example of such a substituted alkyl group is (3-sulfopropyl)acrylic acid ester, potassium salt. Suitable second monomers include 2-acrylamido-2-methylpropane sulfonic acid ($CH_2=CH-CONHC(CH_3)_2-CH_2-SO_3H$) and/or a salt thereof. Suitable salts include the sodium, lithium, potassium, ammonium, and substituted ammonium salts, and mixtures thereof.

In embodiments, the second monomer utilized in a copolymer component of a hydrogel of the present disclosure is 2-acrylamido-2-methylpropane sulfonic acid sodium salt (NaAMPS) ($CH_2=CH-CONHC(CH_3)_2-CH_2-SO_3^-$ $M^+$). Thus, in some embodiments, the first monomer utilized in a copolymer component of a hydrogel of the present disclosure may include a mixture of acrylic acid and sodium acrylate, and the second monomer may include sodium 2-acrylamido-2-methylpropane sulfonate.

The first monomer (acrylic acid and/or salt or salt thereof, calculated as acrylic acid) may be present in an amount of from about 8 weight % to about 85 weight % of copolymer in the hydrogel, in embodiments from about 10 weight % to about 80 weight %, of the total amount of the copolymer in the hydrogel. The second monomer, in embodiments NaAMPS, may be present in an amount of from about 15 weight % to about 92 weight % of the copolymer in the hydrogel, in embodiments from about 20 weight % to about 90 weight % of the copolymer in the hydrogel.

Optionally, an effective amount of a cross-linking agent or mixture of cross-linking agents may be utilized to form the copolymer component of a hydrogel of the present disclosure. An effective amount of cross-linking agent is an amount that produces a conductive composition with the desired physical properties, such as coherence and adhesion, and electrical properties. Although the amount required will depend on, for example, the molecular weight of the cross-linking agent, the number of ethylenically unsaturated, free radical polymerizable groups present in the cross-linking agent, the amount of free radical polymerizable monomers present in the monomer mix, when the cross-linking agent is present, the amount of crosslinking agent will be present in an amount of from about 0.01 weight % to 1 weight % of the copolymer utilized in the hydrogel, in embodiments from about 0.02 weight % to 0.08 weight % of the copolymer utilized in the hydrogel.

Suitable cross-linking agents include free radical polymerizable monomers that possess more than one ethylenically unsaturated, free radical polymerizable group. Numerous crosslinking agents polymerizable by free-radical initiated polymerization are within the purview of those skilled in the art. Crosslinking agents include, for example, bis-acrylamides and methacrylamides, such as N,N'-methylene bis-acrylamide; acrylate and methacrylate esters of polyols, such as, ethylene glycol diacrylate and dimethacrylate, diethylene glycol diacrylate and dimethacrylate, trimethylolpropane triacrylate and trimethacrylate, ethoxylated trimethylolpropane triacrylate and trimethacrylate; pentaerythritol triacrylate and trimethacrylate, pentaerythritol tetraacrylate and tetramethacrylate, and polyethylene glycol diacrylates and dimethacrylates, such as the diacrylates and dimethacrylates of polyethylene glycols having a molecular weight of from about 200 to about 600. In embodiments, a suitable crosslinking agent may include N,N'-methylene bis-acrylamide $[CH_2=CHCONH)_2CH_2]$.

In embodiments, a polymerization initiator may be utilized with the first monomer and second monomer to form a copolymer for use in a hydrogel of the present disclosure. An effective amount of a polymerization initiator may be combined with the monomers to form such a copolymer. As used herein, an effective amount is an amount that produces efficient polymerization of the monomers under polymerization conditions to produce a hydrogel suitable for use as a conductive composition. Numerous free radical polymerization initiators are within the purview of those skilled in the art. The polymerization initiator may be a single compound or a mixture of compounds. Thermal and/or photo free radical polymerization initiators, for example, may be used.

Suitable thermal free radical polymerization initiators include azo compounds, such as 2,2-azobisisobutyronitrile (AIBN). Suitable photo free radical polymerization initiators are disclosed in "Photoinitiators for Free-Radical-Initiated Photoimaging Systems," by B. M. Monroe and G. C. Weed, *Chem. Rev.*, 93, 435-448 (1993) and in "Free Radical Polymerization" by K. K. Dietliker, in *Chemistry and Technology of UV and EB Formulation for Coatings, Inks, and Paints*, P. K. T. Oldring, ed., SITA Technology Ltd., London, 1991, Vol. 3, pp. 59-525. Suitable free radical photo polymerization initiators include, for example, 1-hydroxycyclohexylphenyl ketone (HCPK, IRGACURE® 184); 2-hydroxy-2-methyl-1-phenylpropan-1-one (DAROCUR® 1173); 2-hydroxy-1-[4-(2-hydroxyethoxy)phenyl]-2-methyl-1-propan-1-one (IRGACURE®2959), 2,2-dimethoxy-2-phenylacetophenone (benzildimethyl ketal, BDK, IRGACURE®651), benzophenone, a mixture of 50 weight % benzophenone and 50 weight % of 1-hydroxycyclohexylphenyl ketone (IRGACURE® 500), and combinations thereof.

The polymerization initiator may be present in a copolymer utilized in a hydrogel in an amount less than about 1 weight % of the copolymer, in embodiments less than about 0.7 weight % of the copolymer, in other embodiments less than about 0.4 weight % of the copolymer.

The hydrogel utilized as a conductive composition may also include a neutralizer. Bases such as hydroxides, amines, Lewis bases, and mixtures thereof may be used as neutralizers. Non-limiting examples of neutralizers include ammonium hydroxide, sodium hydroxide, potassium hydroxide, lithium hydroxide, combinations thereof, and the like. If the acrylic acid and/or the second monomer, such as the 2-acrylamido-2-methylpropane sulfonic acid, are included as monomers in forming a copolymer for use in the hydrogel, it may be desirable to add neutralizer to neutralize some of the acid so that the pH of the mixture is from about 3 to about 6.5.

Where utilized, a neutralizer may be present in an amount from about 2 weight % to about 8 weight % of the hydrogel.

In addition to a free radical initiator, small amounts of free radical polymerization inhibitors may be present with one or more of the monomers, and/or the crosslinking agent, and/or may be added to the mixture to prevent premature polymerization of the reaction mixture. Suitable free radical polymerization inhibitors include, for example, hydroquinone, 4-methoxyphenol, di-t-butyl-p-cresol, pyrogallol, t-butyl catechol, benzoquinone, 4,4'-thio-bis-(3-methyl-6-t-butylphenol), and 2,2'-methylene-bis-(4-methyl-6-t-butylphenol). When present, the amount of the polymerization inhibitor may be from about 0.01 weight % to about 5 weight % of the hydrogel.

In some embodiments a thickener may be added to the hydrogel. Suitable thickeners include rheological modifiers which permit tailoring the viscosity of the hydrogel to permit its use as a conductive composition with a medical electrode. Non-limiting examples of such thickeners include silica, gums including xanthan gum, polymers including polyvinyl pyrrolidone (PVP), polyacrylamides, polyacrylic acid (including those sold under the name CARBOPOL®), salts thereof, combinations thereof, and the like. Where utilized, a thickener may be present in a hydrogel of the present disclosure in an amount from about 0.1 weight % to about 8 weight % of the hydrogel, in embodiments from about 0.5 weight % to about 5 weight % of the hydrogel.

An example of a suitable polymer which may be utilized as the hydrogel includes RG-63B, commercially available from Covidien.

In use, such a hydrogel of the present disclosure may contain the polymer or copolymer, and any other additives, including components utilized to form the copolymer, in an amount from about 20% by weight to about 97% by weight of the hydrogel, with the balance being water and/or a humectant.

As noted above, the above gels may be formed by free radical polymerization. Free radical polymerization may be initiated by, for example, heating the mixture when a thermal free radical polymerization initiator is present in the mixture, or exposing the mixture to actinic radiation when a photoinitiated free radical polymerization initiator is present in the mixture. Any convenient source or sources of actinic radiation providing wavelengths in the region of the spectrum that overlap the absorption bands of the photoinitiated free radical polymerization initiator can be used to activate polymerization. The radiation can be natural or artificial, monochromatic or polychromatic, incoherent or coherent, and for high efficiency should correspond closely in wavelengths to the absorption bands of the polymerization initiator. Conventional light sources include fluorescent lamps, mercury vapor lamps, metal additive lamps, and arc lamps. Useful lasers are those whose emissions fall within or overlap the absorption bands of the photoinitiated free radical polymerization initiator. Although, if desired, the mixture may be degassed before polymerization and/or the polymerization may be carried out under an inert atmosphere, it is not necessary to degas the mixture before polymerization or to carry out the polymerization under an inert atmosphere.

Other hydrogels which may be utilized in accordance with the present disclosure include those disclosed in U.S. Pat. Nos. 5,354,790, 5,143,071, 4,657,009 and 4,657,023, the disclosures of each of which are incorporated herein by reference in their entireties for all purposes. For example, hydrogels for use in accordance with the present disclosure may be based upon polyethylene oxide (PEO), polyvinyl pyrrolidone (PVP), natural polysaccharides such as Karaya gum, synthetic polysaccharides, combinations thereof, and the like.

For example, in embodiments, the hydrogel may be formed from a homogeneous aqueous mixture including water and a crosslinked polymer such as polyethylene oxide (PEO). In other embodiments, a hydrogel may be formed from a cohesive uniform mixture of water, an electrolyte, a crosslinked poly(vinyl pyrrolidone) (PVP), and a viscosity-enhancing polymer. It should be noted that these hydrogel compositions may exist as a multiphase system including high molecular weight macromolecules which are present in the uniform mixture. An irradiative crosslinking process may be utilized to form these hydrogels; the irradiation "freezes" in place these microphase regions to provide a stable material.

As noted above, these PEO and/or PVP based hydrogels may be produced by exposing an aqueous mixture of at least one water-soluble high molecular weight linear polymer, e.g., PEO or PVP, to a dose of high energy ionizing radiation, which is effective to form a gel-like material. For example, a homogeneous aqueous mixture of PEO, present at a concentration of from about 7 to about 35 weight %, in embodiments from about 10 to about 25 weight %, may be used. Alternatively, an aqueous mixture of PVP and a viscosity-enhancing hydrophilic polymer may be employed. It has been found that irradiation of these polymeric mixtures produce gels which are cohesive, adhesive, sufficiently tacky, and yet non-stringy.

For a conductive formulation, the homogeneous aqueous mixtures described above may be prepared with an effective amount of a water-soluble electrolyte. Irradiation of these electrolyte-containing mixtures may produce conductive sheets having the desired non-stringy surface properties.

PVPs which may be used for forming a hydrogel in accordance with the present disclosure may include a polymer of N-vinyl-2-pyrrolidone having a weight average molecular weight ($M_w$) of from about 200 kD to about 2,000 kD, in embodiments from about 500 kD to about 1,500 kD, in embodiments from about 750 kD to about 1,250 kD.

Homogeneous aqueous mixtures having from about 7 to about 35 weight percent of PVP, in embodiments from about 10 to about 25 weight percent of PVP, may be suitable for forming hydrogels.

Irradiation crosslinking of PVP mixtures may occur utilizing means within the purview of those skilled in the art, including those disclosed in U.S. Pat. No. 4,699,146, the entire disclosure of which is incorporated herein by reference in its entirety for all purposes.

In embodiments, a hydrophilic polymer, having a weight average molecular weight in excess of about 100 kilodaltons, may be added to the mixture in amounts from about 0.5 weight percent to about 4 weight percent of the mixture. This hydrophilic polymer can enhance the viscosity of the conductive polymeric mixture such that the final viscosity is restored to a degree providing coatable, extrudable viscous aqueous polymeric mixtures. Furthermore, when exposed to radiant energy at an effective dose, a film of the extrudable aqueous mixture is transformed into a cohesive gel-like solid having the desirable highly conductive adhesive properties of the hydrogels.

As stated above, the viscosity-enhancing hydrophilic polymer should have a sufficiently high weight average molecular weight, $M_W$. In general, such a polymer should have a $M_W$ in excess of about 100 kD, in embodiments as high as 15 million daltons. Such a polymer may be derived from natural, synthetic, or semisynthetic sources; it may be linear, branched, crosslinked, noncrosslinked, water-soluble, or water insoluble, so long as it is hydrophilic in nature.

Examples of suitable synthetic materials useful as viscosity-enhancers include, but are not limited to, polyacrylamide, poly(vinyl alcohol), a polyacrylate salt, poly(ethylene oxide), poly(ethylene imine), polyacrylamide sulfonic acid or their salts, polyacrylonitrile, hydrophilic derivatives, mixtures, blends, or copolymers thereof. In embodiments, the hydrophilic polymer utilized as a viscosity enhancer may be a poly(ethylene oxide) having a $M_W$ of from about 500 to about 10,000 kD, in embodiments about 900 kD.

In embodiments, a suitable semisynthetic polymer which may be used as a viscosity-enhancer includes a derivative of cellulose. For example, methylcellulose, ethylcellulose, carboxymethylcellulose, hydroxyethylcellulose, combinations thereof, and the like, may be used. In some cases, a carboxymethylcellulose (CMC) having a weight average molecular weight of about 700,000 daltons, may be used.

Other suitable macromolecules which may be used as a viscosity-enhancer include those derived from natural sources, such as starch, agar, dextran, dextrin, carrageenan, xanthan, guar, their derivatives, or combinations thereof.

The above viscosity-enhancers may be added to an aqueous electrolyte-PVP mixture in amounts of from about 1 weight % to about 2 weight % of the mixture. Their inclusion may increase the viscosity of the mixture to at least about 8,000 centipoise (cPs), in embodiments from about 10,000 cPs to about 20,000 cPs.

The poly(vinyl pyrrolidone) formulations useful in these applications include those incorporating and binding high concentrations of water while maintaining adequate surface tack (adhesiveness), sufficient strength (cohesiveness), and substantial non-stringiness. The polymer/salt/viscosity-enhancer/water mixture should be viscous enough to be extrudable and to form into a sheet-like configuration, e.g., a liquid film of about 0.1 to about 2 mm thickness, before crosslinking. In embodiments, the viscosity of the aqueous mixtures exceed about 8,000 cps.

After the viscous mixture is applied or cast to the desired thickness, it is then subjected to crosslinking high energy irradiation, such as a high energy electron flux as produced by an electron accelerator or Van De Graaf generator, to form a hydrogel. In general, alpha particles, beta particles, gamma rays, X-rays, electron beams, or high energy ultraviolet radiation may be used to initiate or precipitate the crosslinking of polymer chains. The major requirement is that the beam of electrons be of sufficient energy to completely penetrate the mixture, so that the mixture receives a radiation dose effective to crosslink the entire cross section of the sample. Proper dose/energy/thickness relationships are within the purview of those skilled in the art of radiation processing. To achieve the desired degree of uniform crosslinking, doses of from about 0.5 Mrads to about 4.5 Mrads, in embodiments from about 0.6 Mrads to about 2 Mrads, in embodiments from about 0.7 Mrads to about 1.8 Mrads may be utilized, depending upon the selected polymer, its concentration, viscosity-enhancer and its concentration, the selected salt and its concentration, and the presence or absence of any functional, therapeutic agents, or other additives.

The formation of a polyethylene oxide formulation is similar to those described above for a PVP formulation. Suitable PEO polymers for use in forming a hydrogel in accordance with the present disclosure may have molecular weights from about 200 kilodaltons (kD) to about 5,000 kD, in embodiments from about 750 kD to about 3,000 kD, in other embodiments from about 1,000 kD to about 2,500 kD.

Useful PEOs include those incorporating and binding high concentrations of water while maintaining adequate surface tack (adhesiveness), to avoid leaving a residue. The starting water soluble linear polyethylene oxide should have a molecular weight high enough to form a viscous solution for processing and readily crosslink. Generally, polymers with weight average molecular weights ($M_W$) of from about $0.2 \times 10^6$ to about $10 \times 10^6$ Daltons, in embodiments from about $0.5 \times 10^6$ to about $5 \times 10^6$ Daltons, may be used. The concentration of polymer may be from about 3 to about 35 weight %, in embodiments from about 4 to about 20 weight %, of the overall mixture, depending upon its molecular weight. In embodiments, the concentration of polymer may be less than about 35%, so that the polymer may not be overly brittle. The polymer water solution should be viscous enough to form into a sheet-like configuration, e.g., a liquid film of about 0.2 to 4 mm thickness, before crosslinking. Illustrative viscosities are from about 2,000 to 2,000,000 cPs.

A continuous sheet of hydrophilic gel of from about 10 to about 150 mils (0.254-381 mm) may be formed. After the viscous solution is applied or cast to the desired thickness, it is then subjected to crosslinking high energy irradiation, such as a high energy electron flux as produced by an electron accelerator. If conditions are selected which exclude atmospheric oxygen, gamma radiation may be used. The major requirement is that the beam of electrons be of sufficient energy to completely penetrate the solution, so that the solution receives a radiation dose effective to crosslink the entire cross section of the sample. Proper dose/energy/thickness relationships are within the purview of those skilled in the art. To achieve the desired degree of uniform crosslinking, i.e., effective to convert the viscous polymer solution into a viscoelastic solid gel, doses of from about 0.20 to about 5.0 Mrads, in embodiments from about 0.75 to about 2.0 Mrads, may be used, depending upon the selected polymer molecular weight, and its concentration, any functional or therapeutic additives included in the viscous polymer solution, and the like. Generally, higher polymer concentrations require high irradiation doses to produce an acceptable viscoelastic solid gel.

In other embodiments, the hydrogel may be formed from naturally occurring materials such as gum karaya, gum acacia, locust bean gum and other polysaccharides, and synthetically formulated polysaccharides such as guar and celluloses including cellulose derivatives such as carboxymethyl cellulose, as well as combinations thereof. The hydrogel may also be formed from synthetic polymers such as polyacrylamide and its congeners, as well as polyacrylic acids. Such synthetic polymers may have weight average molecular weights ($M_W$) of from about 250,000 to about 4,000,000, in embodiments from about 450,000 to about 1,000,000. When monomers such as acrylic acid or acrylamide are polymerized, it may be desirable to use activators in the formation of the hydrogels. Activators, which may be used during polymerization include ferrous sulfate, sodium metabisulfite, potassium persulfate, combinations thereof, and the like. Suitable amounts of activators are within the purview of those skilled in the art.

The synthetic polymers and/or synthetic or natural gums and other polysaccharides may form a solid phase of the matrix forming the hydrogel. The liquid phase of the matrix forming the hydrogel may include hydric alcohols such as glycerol and/or propylene glycol, and/or water, most commonly water. Solutions or emulsions of saccharides and/or polysaccharides and/or proteins may be used to plasticize the matrix forming the hydrogel. Alternatively, a combination of a solution or emulsion of polysaccharides, saccharides or proteins may be used in the liquid phase of the matrix forming the hydrogel.

The hydrogel thus includes a gel phase including a synthetic polymer mixture, a large molecular weight polysaccharide matrix, and/or a matrix including a large molecular weight polysaccharide in combination with a synthetic polymer. The hydrogel may have a solids content of from about 2% to about 50% by weight of the hydrogel, in embodiments from about 10% to about 40% by weight of the hydrogel. The liquid phase of the hydrogel, including water, may be present in an amount of from about 50% to about 98% by weight of the hydrogel, in embodiments from about 60% to about 90% by weight of the hydrogel.

In embodiments, a vinyl acetate dioctyl maleate copolymer may be used in forming the hydrogel. In other embodiments, suitable gum materials which may be used in forming the hydrogel include starch graft copolymers derived from corn starch and acrylonitrile, including graft terpolymers of starch, acrylamide and sodium acrylate known as starch-g-poly(acrylamide-co-sodium acrylate). The starch-g-poly(acrylamide-co-sodium acrylate) material may be used alone to form the substrate or it may be used in combination with a synthetic gum such as acrylamide or a natural gum such as karaya.

The monomers and any additional components described above for forming a hydrogel may be mixed and spread or coated as a layer on a release liner, for example a siliconized release substrate such as silicone coated polyethylene terephthalate film, or other substrate prior to polymerization. In other embodiments, the hydrogel may be formed and then applied to a release liner and/or substrate for use with an electrode.

As noted above, a variety of electrolytic substances may be added to the mixtures in amounts sufficient to produce conductive products. Suitable electrolytes include ionizable inorganic salts, organic compounds, or combinations of both. Examples of such salts include, but are not limited to, lithium chloride, magnesium chloride, sodium chloride, potassium chloride, magnesium acetate, ammonium acetate, monoethanolamine acetate, diethanolamine acetate, sodium lactate, sodium citrate, ammonium sulfate, magnesium sulfate, calcium sulfate, combinations thereof, and the like. The electrolyte should be stable and inert upon dissolving in any aqueous mixture utilized to form a hydrogel, and any subsequent radiation crosslinking step for those hydrogels formed thereby. Although virtually any amount of electrolyte may be present in the hydrogel, it may be desirable to have the electrolyte present at a concentration of from about 0.1 to about 15 weight % of the hydrogel, in embodiments from about 0.7 to about 10 weight % of the hydrogel, in embodiments from about 1 weight % to about 8 weight % of the hydrogel.

Following polymerization of the components utilized to form a hydrogel, the resulting conductive composition may transferred to a conductive substrate. Alternatively, the conductive composition may be adhered to a conductive substrate, and the release liner left in place to protect the conductive composition until it is ready for use.

Sensation Enhancing Component

In accordance with the present disclosure, a hydrogel utilized with an electrode of the present disclosure also possesses one or more components which may be utilized to provide either a cooling or warming sensation upon placement on a patient's skin, optionally upon the introduction of electrical stimulation. Such a component may be referred to, in embodiments, as a sensation enhancing component. The sensation enhancing component may be added to the monomers utilized to form the hydrogel, thereby becoming incorporated within the gel portion of the hydrogel matrix upon polymerization. A sensation enhancing component may also be imbibed in the hydrogel after formation of the gel. Alternatively, a sensation enhancing component may be added to a polymer mix prior to crosslinking with ionizing radiation or prior to thermoset gel formation.

As noted above, in embodiments, the sensation enhancing component may provide a cooling effect and/or sensation upon use and may be referred to, in embodiments, as a cooling component. Examples of suitable cooling components include, but are not limited to, menthol, camphor, eucalyptol, icilin, methyl lactate, N-ethyl-p-menthane-3-carboxamide, combinations thereof, and the like. Where utilized, the cooling component may be present in a hydrogel of the present disclosure utilized with an electrode in an amount of from about 0.01% by weight to about 20% by weight of the hydrogel, in embodiments from about 0.5% by weight to about 10% by weight of the hydrogel, in embodiments from about 1% by weight to about 5% by weight of the hydrogel. In embodiments, menthol may be present in a hydrogel of the present disclosure utilized with an electrode in an amount of about 20% or less to reduce skin irritation.

In other embodiments, the sensation enhancing component may provide a warming effect and/or sensation upon use and may be referred to, in embodiments, as a warming component. Examples of suitable warming components include, but are not limited to, capsaicin, nonivamide, cinnamaldehyde, combinations thereof, and the like. Where utilized, the warming component may be present in a hydrogel of the present disclosure utilized with an electrode in an amount of from about 0.01% by weight to about 1% by weight of the hydrogel, in embodiments from about 0.1% by weight to about 1% by weight of the hydrogel, in embodiments from about 0.5% by weight to about 1% by weight of the hydrogel.

The conductive composition, including at least one hydrogel and at least one component capable of providing either a cooling or warming sensation upon electrical stimulation, may be pleasing to a patient to which an electrode of the present disclosure has been applied. A patient experiencing a cooling or warming sensation may also communicate this sensation to a health care provider, thereby providing feedback to the health care provider that the electrode is, indeed, correctly applied and functioning as intended.

Other Additives

Other conventional ingredients of conductive compositions may be present in the hydrogel. For example, humectants and medicinal agents, including antimicrobials, antiseptics, analgesics, disinfectants, and the like, may be added to a hydrogel. Suitable additives include, but are not limited to, *aloe, centella asiatica, echinacea, ginkgo biloba*, ginseng, hyssop, combinations thereof, and the like. Such additional additives may be present in a hydrogel of the present disclosure utilized with an electrode in an amount of from about 0.1% by weight to about 10% by weight of the hydrogel, in embodiments from about 0.5% by weight to about 5% by weight of the hydrogel, in embodiments from about 1% by weight to about 4% by weight of the hydrogel. In embodiments, such additional additives may be present in a hydrogel of the present disclosure utilized with an electrode in an amount of about 3%.

Water is present in the mixture. The amount of water includes any water present in any of the ingredients and any water added with ingredients that are in water solution, such as the monomers, the crosslinking agent, the neutralizer, etc. In embodiments, humectants may be added to the water phase of a hydrogel utilized as a conductive composition in an electrode of the present disclosure. Humectants which may be used include non-volatile, non-toxic, water soluble or water miscible viscous liquids at room temperature. Suitable humectants include, but are not limited to, polyhydric alcohols such as glycerol, sorbitol, ethylene glycol, propylene glycol, polyethylene glycols (PEG) of varying molecular weights including PEG 300, PEG 400 and PEG 600, polypropylene glycols, combinations thereof, and the like. The humectant may be utilized in combination with water or without water. Where utilized with water, the ratio of water to humectant may be from about 1:10 to about 10:1.

As noted above, in some embodiments, a hydrogel of the present disclosure may contain the polymer or copolymer and any other additives described herein in an amount from about 20% by weight to about 97% by weight, with the balance being water and/or a humectant in an amount from about 3% to about 80% by weight of the hydrogel.

Exemplary Formulations

The Tables below provide exemplary hydrogels of the present disclosure, which include the above warming or cooling components described above. These formulations are for illustration only; the present disclosure is not limited thereto.

TABLE 1

Hydrogel with 5% Menthol (E-Beam Cured)

| Compound | Weight % |
| --- | --- |
| Water | 90.84 |
| Polyox 301 | 3.70 |
| Methyl paraben | 0.20 |
| Propyl paraben | 0.05 |
| PEI Corcat P-600 | 0.21 |
| Menthol | 5.00 |
| | 100.00 |

Polyox 301 = an ethylene oxide having a molecular weight of about 400,000, commercially available from Union Carbide
PEI Corcat P-600 = a polyethylimine having a molecular weight of from about 40,000 to about 60,000, commercially available from Cordova Chemcial.

TABLE 2

Hydrogel with Menthol, Camphor, Aloe (E-Beam Cured)

| Compound | Weight % |
| --- | --- |
| Water | 89.74 |
| Polyox 301 | 3.70 |
| Methyl paraben | 0.20 |
| Propyl paraben | 0.05 |
| PEI Corcat P-600 | 0.21 |
| Menthol | 3.00 |

TABLE 2-continued

Hydrogel with Menthol, Camphor, Aloe (E-Beam Cured)

| Compound | Weight % |
| --- | --- |
| Camphor | 3.00 |
| Aloe | 0.10 |
| | 100.00 |

Polyox 301 = is an ethylene oxide having a molecular weight of about 400,000 commercially available from Union Carbide
PEI Corcat P-600 = a polyethylimine having a molecular weight of from about 40,000 to about 60,000, commercially available from Cordova Chemcial.

TABLE 3

Hydrogel with 3% Menthol (UV Cured)

| Compound | Weight % |
| --- | --- |
| 58% NaAMPS soln. | 46.34 |
| 1% MBA in DI water | 3.04 |
| Acrylic acid | 2.84 |
| Glycerol | 41.61 |
| 50% NaOH in $H_2O$ soln. | 0.12 |
| Silica | 2.54 |
| 3% Irg.184 in 2-PrO | 0.51 |
| Menthol | 3.00 |
| | 100.00 |

1% MBA in DI water = 1% N,N'-methylene bis-acrylamide in deionized water
3% Irg.184 in 2-PrOH = 3% 1-hydroxycyclohexylphenyl ketone (commercially available as IRGACURE ® 184) in 2-propanol

TABLE 4

Hydrogel with 2% Menthol (UV Cured)

| Compound | Weight % |
| --- | --- |
| 58% NaAMPS soln. | 46.34 |
| 1% MBA in DI water | 3.04 |
| Acrylic acid | 2.84 |
| Glycerol | 42.61 |
| 50% NaOH in $H_2O$ soln. | 0.12 |
| Silica | 2.54 |
| 3% Irg.184 in 2-PrOH | 0.51 |
| Menthol | 2.00 |
| | 100.00 |

1% MBA in DI water = 1% N,N'-methylene bis-acrylamide in deionized water
3% Irg.184 in 2-PrOH = 3% 1-hydroxycyclohexylphenyl ketone (commercially available as IRGACURE ® 184) in 2-propanol Medical Electrodes Medical electrodes transmit electrical signals or currents to or from a patient's skin and an external medical apparatus. Medical electrodes are within the purview of those skilled in the art. These electrodes may include a conductive composition such as a hydrogel of the present disclosure on a substrate. The layer of conductive composition can be adhered to or contacted with the skin of the patient. The medical electrode may also include a conductive interface that is electrically connected to the layer of conductive composition and adapted to be electrically connected to an item of external medical equipment. For many applications, the conductive composition should be sufficiently adhesive to adhere to the patient's skin, i.e., be a conductive adhesive. The configuration of the electrode and the adhesive properties required will depend on the intended application, such as whether the electrode is a transmission electrode, i.e., an electrode that sends electric currents or signals to the patient's body, or a sensing or monitoring electrode, i.e., an electrode that sends electrical signals from the patient's body to external medical equipment.

Figure 2:
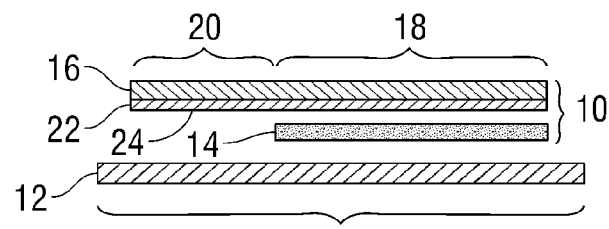
FIG. 2 is a cross-sectional view of the medical electrode of FIG. 1.

FIG. 1 and FIG. 2 show a medical electrode 10 on release liner 12. Release liner 12 is a release paper or film of a waxed or coated plastic, such as a silicone coated polyethylene terephthalate film, which may be used to protect medical electrode 10 before application of the electrode to a skin surface.

Electrode 10 includes a layer of a hydrogel of the present disclosure as conductive composition 14. Electrode 10 also includes conductive interface 16 having a conductor member with a conductive portion 18 contacting layer of conductive composition 14 and tab portion 20 extending beyond layer of conductive composition 14 for mechanical and electrical contact with external medical equipment, such as a electrocardiogram monitoring (ECG) machine, an electroencephalogram (EEG) machine, or a transcutaneous electrical nerve stimulation (TENS) machine (not shown). Conductive interface 16 includes conductive layer 24, coated on at least side 22 of conductive interface 16. Conductive layer 24 contacts layer of conductive composition 14. Medical electrode 10 can be used either as a diagnostic electrocardiogram (ECG or EKG) electrode or as a transcutaneous electrical nerve stimulation (TENS). In use, release liner 12, if present, is removed. The layer of conductive composition 14 of electrode 10 is applied to the surface of the patient's skin and electrically connected to the external medical equipment.

Figure 3:
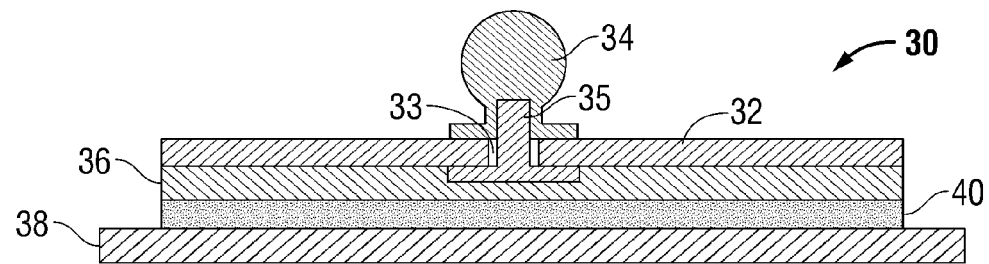
FIG. 3 is a cross-sectional view of a snap medical electrode.

FIG. 3 shows a cross-section of snap medical electrode 30 on a release liner. Electrode 30 has nonconductive backing 32, which has opening 33 covered by snap 34 through which eyelet 35 protrudes. Snap 34 is secured to eyelet 35. Together snap 34 and eyelet 35 provide at least part of a conductive interface adapted to provide an electrical connection between a flexible conductive layer 36 and the external medical equipment (not shown). Eyelet 34 and backing 32 are covered by flexible conductive layer 36 which, in embodiments, may be made of a material such as carbon vinyl. A hydrogel of the present disclosure may be utilized as a conductive composition 40 and adhered to conductive layer 36. Alternatively, a hydrogel of the present disclosure may be utilized as a conductive composition 40 and adhered to backing 32, thereby omitting conductive layer 36. Release liner 38 protects the conductive composition 40 prior to use. In embodiments, a complete or partial layer of silver and/or a silver salt such as silver chloride may be placed between conductive composition 40 and conductive layer 36 (not shown).

In addition, in embodiments, conductive layer 36 and non-conductive layer 32 may possess contiguous windows adjacent each other in each layer (not shown) permitting the visualization of conductive composition 40 during use so that changes in color, opacity, and the like may be observed with an electrode in place on a patient.

Figure 4:
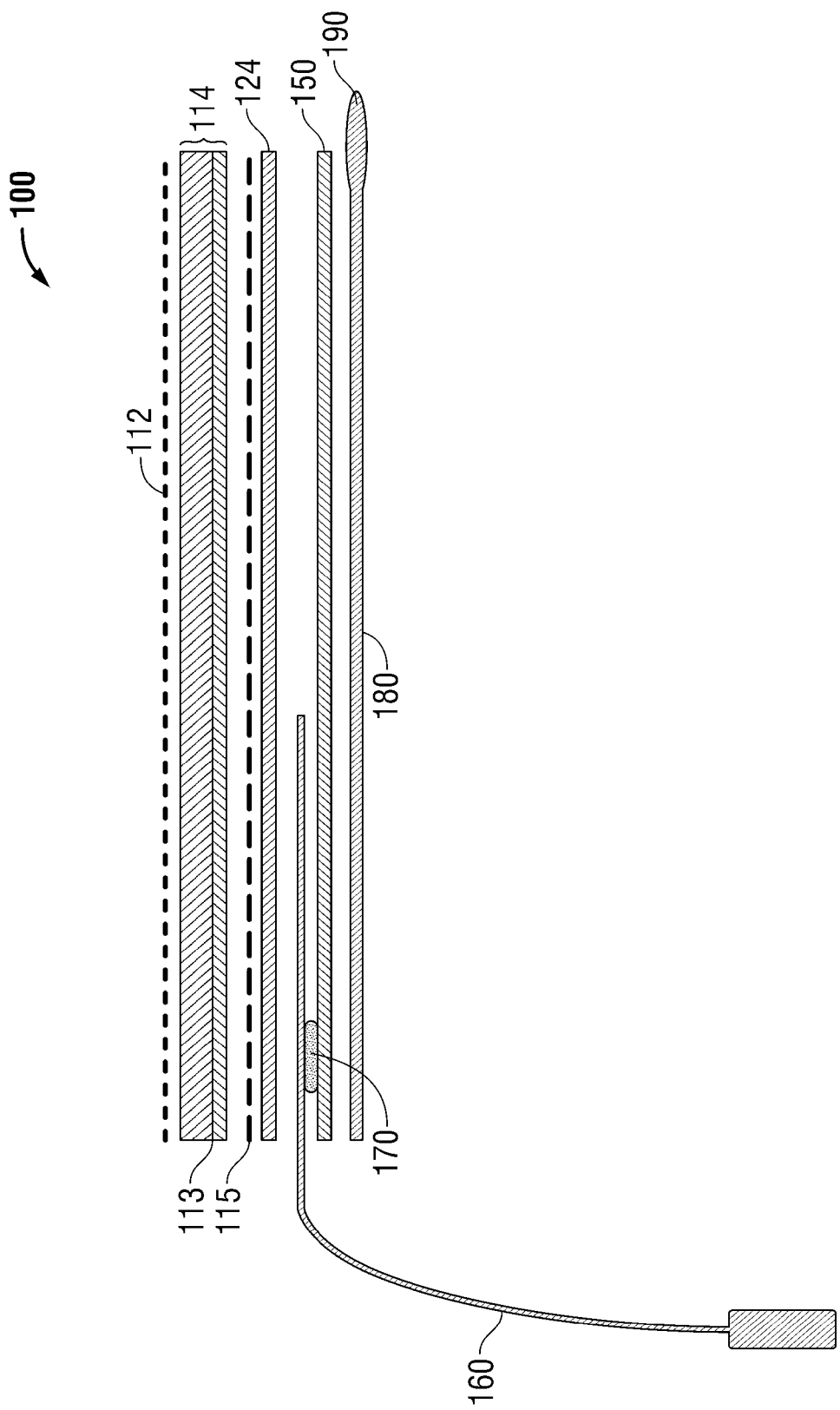
FIG. 4 is a cross-sectional view of an alternate medical electrode of the present disclosure.

FIG. 4 shows a cross-section of an alternate medical electrode 100 on a release liner 112, which may be a polyester film or any other material suitable for use as a release liner. Electrode 100 includes a layer of a hydrogel of the present disclosure as conductive composition 114. In embodiments, conductive composition 114 may have a reinforcement member 113 embedded in the hydrogel, which may be a woven or a non-woven mesh or any other material, such as a scrim, suitable for forming a reinforcement member. Electrode 100 may also possess a conductive layer 124, which may, in embodiments, be a suitable material such as a conductive carbon film of suitable thickness, in embodiments about 2 mil. In some embodiments, a flood coat or a partial coating of silver ink 115 (which can be silver and/or silver chloride) may be between conductive layer 124 and conductive composition 114, applied as a coating on at least a portion of a surface of conductive layer 124. In embodiments, the electrode may include silver (Ag) or silver/silver-chloride (Ag/AgCl) disposed on at least a portion of the first and/or second sides of the conductive layer.

Electrode 100 may also possess a standard stainless steel, tin/copper, or nickel plated pig tail lead wire 160 of a suitable length, in embodiments from about 5 to about 15 inches long, in other embodiments about 9 inches long. Lead wire 160 may possess an insulation jacket which, in turn, may be bound to conductive layer 124 using an adhesive 170. Electrode 100 may also possess a reinforcement film 150 having a medical grade pressure sensitive adhesive (PSA) thereon overlying lead wire 160 and affixing reinforcement film 150 to both conductive layer 124 and cover material 180. Finally, cover material 180 may possess pull tab 190 notched out of cover material 180 on the end of electrode 100 opposite the end into which the lead wire 160 enters the electrode.

Medical electrodes may be packaged for use in any suitable materials within the purview of those skilled in the art. For example, electrodes may be packaged in materials such as polyethylene or other plastic films, foil barrier packaging, combinations thereof, and the like.

INDUSTRIAL APPLICABILITY

The conductive compositions of the present disclosure may be useful with medical electrodes that can be used with medical equipment for a variety applications, such as: electrocardiogram monitoring (ECG) electrodes (tab and snap style) for monitoring heart activity and for diagnosing heart abnormalities; electroencephalogram (EEG) electrodes; transcutaneous electrical nerve stimulation (TENS) electrodes used for pain management; neuromuscular stimulation (NMS) used for treating conditions such as scoliosis; muscle stimulation electrodes; wound treatment electrodes (accelerated healing of skin wounds or broken bones); defibrillation electrodes to dispense electrical energy to a chest cavity of a mammalian patient to defibrillate heart beats of the patient; iontophoresis; and dispersive electrodes to receive electrical energy dispensed into an incision made during electrosurgery. Other applications of the conductive compositions of the invention include, for example, electrosurgical dispersive pads; drug delivery (passive or iontophoretic); pre-surgical limb or area markers, tapes (anchoring chest tubes, NG tubes, IVs, cannulae, etc); and sterile seals at needle or cannula entry points. The medical equipment used in these applications is within the purview of those skilled in the art. The presence of one or more heat or cool sensation enhancing components may aid in the dilation or contraction of pores in the skin, and may enhance signal pickup and/or control skin permeability.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, or material.

What is claimed is:

1. A conductive composition comprising:
   a conductive hydrogel formed of a crosslinked polymer;
   at least one component capable of providing a patient with a sensation selected from the group consisting of warming and cooling upon contact with tissue of a patient; and
   an additive selected from the group consisting of *aloe, centella asiatica, echinacea, ginkgo biloba*, ginseng, hyssop, and combinations thereof.

2. The conductive composition of claim 1, wherein the conductive hydrogel comprises a component selected from the group consisting of gelatin, polysaccharides, crosslinked acrylamide polymers, hydroxyethylmethacrylate polymers, crosslinked polyhydroxyethylacrylate, polymerized, crosslinked 2-acrylamido-2-methylpropane sulfonic acid polymers, crosslinked polyvinylpyrrolidone, polyacrylic acid, copolymers of the foregoing, one or more salts thereof, and combinations thereof.

3. The conductive composition of claim 1, wherein the conductive hydrogel comprises a copolymer comprising a first monomer comprising a mixture of acrylic acid and a salt thereof, present in an amount of from about 8 weight % to about 85 weight % of the hydrogel, and a second monomer of the formula $CH_2=CHC(O)XR$, in which X is O or NH and R is an unsubstituted or substituted alkyl group of from about 1 to about 5 carbon atoms present in an amount of from about 15 weight % to about 92 weight % of the conductive hydrogel.

4. The conductive composition of claim 1, wherein the conductive hydrogel comprises a homogeneous mixture of water and the crosslinked polymer present at a concentration of from about 7 percent by weight to about 35 percent by weight of said homogeneous mixture, said crosslinked polymer having a weight average molecular weight of from about 200 kD to about 5,000 kD.

5. The conductive composition of claim 4, wherein said crosslinked polymer comprises poly(ethylene oxide).

6. The conductive composition of claim 4, wherein said crosslinked polymer comprises poly(vinyl pyrrolidone) and a viscosity-enhancing hydrophilic polymer having a weight average molecular weight in excess of about 100 kD present at a concentration of from about 1 to about 2 percent by weight of said homogeneous mixture, the viscosity-enhancing hydrophilic polymer selected from the group consisting of polyacrylamide, poly(vinyl alcohol), polacrylate, poly(ethylene oxide), poly(ethylene imine), carboxymethylcellulose, methylcellulose, cellulose derivatives, polyacrylamide sulfonic acid, polyacrylonitrile, agar, dextran, dextrin, carageenan, xanthan, guar, derivatives, mixtures, blends, and copolymers thereof.

7. The conductive composition of claim 1, wherein the at least one component capable of providing a patient with a sensation selected from the group consisting of warming and cooling comprises a warming component selected from the group consisting of capsaicin, nonivamide, cinnamaldehyde, and combinations thereof, present in an amount of from about 0.01% by weight to about 1% by weight of the conductive hydrogel.

8. The conductive composition of claim 1, wherein the at least one component capable of providing a patient with a sensation selected from the group consisting of warming and cooling comprises a cooling component selected from the group consisting of menthol, camphor, eucalyptol, icilin, methyl lactate, N-ethyl-p-menthane-3-carboxamide, and combinations thereof, present in an amount of from about 0.01% by weight to about 20% by weight of the conductive hydrogel.

9. The conductive composition of claim 1, wherein the conductive hydrogel further comprises an electrolyte present in an amount of from about 0.1% by weight to about 15% by weight of the conductive hydrogel.

10. The conductive composition of claim 1, wherein the conductive hydrogel further comprises a neutralizer selected from the group consisting of ammonium hydroxide, sodium hydroxide, potassium hydroxide, lithium hydroxide, and combinations thereof.

11. The conductive composition of claim 1, wherein the conductive hydrogel further comprises a cross linking agent selected from the group consisting of N—N'-methylene bis-acrylamide, diethylene glycol diacrylate, diethylene glycol dimethacrylate, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, polyethylene glycol diacrylate, polyethylene glycol dimethacrylate, and combinations thereof.

12. The conductive composition of claim 1, wherein the conductive hydrogel further comprises a polymerization initiator selected from the group consisting of 2,2-azobisisobutyronitrile, 1-hydroxycyclohexylphenyl ketone, 2-hydroxy-2-methyl-1-phenylpropan-1-one, 2-hydroxy-1-[4-(2-hydroxyethoxy)phenyl]-2-methyl-1-propan-1-one, 2,2-dimethoxy-2-phenylacetophenone, benzophenone, and combinations thereof.

13. A conductive composition comprising:
   a conductive hydrogel formed of a crosslinked polymer;
   at least one component capable of providing a patient with a sensation selected from the group consisting of warming and cooling upon contact with tissue of a patient; and
   an additive selected from the group consisting of *centella asiatica, echinacea, ginkgo biloba*, ginseng, hyssop, and combinations thereof,
   wherein the warming component is selected from the group consisting of nonivamide, cinnamaldehyde, and combinations thereof, and
   wherein the cooling component is selected from the group consisting of icilin, methyl lactate, and combinations thereof.

14. The conductive composition of claim 13, wherein the conductive hydrogel comprises a component selected from the group consisting of gelatin, polysaccharides, crosslinked acrylamide polymers, hydroxyethylmethacrylate polymers, crosslinked polyhydroxyethylacrylate, polymerized, crosslinked 2-acrylamido-2-methylpropane sulfonic acid polymers, crosslinked polyvinylpyrrolidone, polyacrylic acid, copolymers of the foregoing, one or more salts thereof, and combinations thereof.

15. The conductive composition of claim 13, wherein the conductive hydrogel comprises a copolymer comprising a first monomer comprising a mixture of acrylic acid and a salt thereof, present in an amount of from about 8 weight % to about 85 weight % of the hydrogel, and a second monomer of the formula $CH_2=CHC(O)XR$, in which X is O or NH and R is an unsubstituted or substituted alkyl group of from about 1 to about 5 carbon atoms present in an amount of from about 15 weight % to about 92 weight % of the conductive hydrogel.

16. The conductive composition of claim 13, wherein the conductive hydrogel comprises a homogeneous mixture of water and the crosslinked polymer present at a concentration of from about 7 percent by weight to about 35 percent by weight of said homogeneous mixture, said crosslinked polymer having a weight average molecular weight of from about 200 kD to about 5,000 kD.

17. The conductive composition of claim 16, wherein said crosslinked polymer comprises poly(ethylene oxide).

18. The conductive composition of claim 16, wherein said crosslinked polymer comprises poly(vinyl pyrrolidone) and a viscosity-enhancing hydrophilic polymer having a weight average molecular weight in excess of about 100 kD present at a concentration of from about 1 to about 2 percent by weight of said homogeneous mixture, the viscosity-enhancing hydrophilic polymer selected from the group consisting of polyacrylamide, poly(vinyl alcohol), polacrylate, poly(ethylene oxide), poly(ethylene imine), carboxymethylcellulose, methylcellulose, cellulose derivatives, polyacrylamide sulfonic acid, polyacrylonitrile, agar, dextran, dextrin, carageenan, xanthan, guar, derivatives, mixtures, blends, and copolymers thereof.

19. The conductive composition of claim 13, wherein the warming component is present in an amount of from about 0.01% by weight to about 1% by weight of the conductive hydrogel.

20. The conductive composition of claim 13, wherein the cooling component is present in an amount of from about 0.01% by weight to about 20% by weight of the conductive hydrogel.

21. The conductive composition of claim 13, wherein the conductive hydrogel further comprises an electrolyte present in an amount of from about 0.1% by weight to about 15% by weight of the conductive hydrogel.

22. The conductive composition of claim 13, wherein the conductive hydrogel further comprises a neutralizer selected from the group consisting of ammonium hydroxide, sodium hydroxide, potassium hydroxide, lithium hydroxide, and combinations thereof.

23. The conductive composition of claim 13, wherein the conductive hydrogel further comprises a cross linking agent selected from the group consisting of N—N'-methylene bis-acrylamide, diethylene glycol diacrylate, diethylene glycol dimethacrylate, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, polyethylene glycol diacrylate, polyethylene glycol dimethacrylate, and combinations thereof.

24. The conductive composition of claim 13, wherein the conductive hydrogel further comprises a polymerization initiator selected from the group consisting of 2,2-azobisisobutyronitrile, 1-hydroxycyclohexylphenyl ketone, 2-hydroxy-2-methyl-1-phenylpropan-1-one, 2-hydroxy-1-[4-(2-hydroxyethoxy)phenyl]-2-methyl-1-propan-1-one, 2,2-dimethoxy-2-phenylacetophenone, benzophenone, and combinations thereof.

25. The conductive composition of claim 13, wherein the additive is present in an amount from about 0.1% by weight to about 10% by weight of the conductive hydrogel.

* * * * *